United States Patent [19]

Okazaki et al.

[11] Patent Number: 5,225,583
[45] Date of Patent: Jul. 6, 1993

[54] ALKYL-ARYL 1,3-PROPANEDIONE SILICONE DERIVATIVE AND AN EXTERNAL PREPARATION FOR SKIN WITH THE DERIVATIVE COMPOUNDED THEREIN

[75] Inventors: Tomomi Okazaki; Kenichi Umishio; Keiichi Uehara, all of Yokohama, Japan

[73] Assignee: Shiseido Co., Ltd., Japan

[21] Appl. No.: 929,123

[22] Filed: Aug. 13, 1992

[30] Foreign Application Priority Data

Aug. 16, 1991 [JP] Japan .................. 3-231228

[51] Int. Cl.$^5$ .................. C07F 7/08; C07F 7/18
[52] U.S. Cl. .................. 556/436; 424/59
[58] Field of Search .................. 556/436

[56] References Cited

U.S. PATENT DOCUMENTS

| | | | |
|---|---|---|---|
| 3,410,822 | 11/1968 | Wihkus et al. | 556/436 X |
| 3,489,781 | 1/1970 | Wihkus et al. | 556/436 |
| 4,467,082 | 8/1989 | Shiroliata et al. | 556/436 X |
| 4,661,611 | 4/1987 | Narang et al. | 556/436 X |
| 4,812,214 | 3/1989 | Wright | 556/436 X |
| 4,880,705 | 11/1989 | Wright | 556/436 X |
| 5,025,053 | 6/1991 | Caruivene et al. | 556/436 X |

FOREIGN PATENT DOCUMENTS

| | | |
|---|---|---|
| 0383655 | 8/1989 | European Pat. Off. . |
| 0354146 | 2/1990 | European Pat. Off. . |

Primary Examiner—Paul F. Shaver
Attorney, Agent, or Firm—Townsend, Snider & Banta

[57] ABSTRACT

Alkyl-aryl 1,3-propanedione silicone derivative characterized in that said derivative is siloxane having at least one unit expressed by the general formula 1 as shown below and other unit which can exist in said siloxane is expressed by a general formula of $O_{4-r/2}SiR^5{}_r$, and an external preparation for skin with said derivative compounded therein.

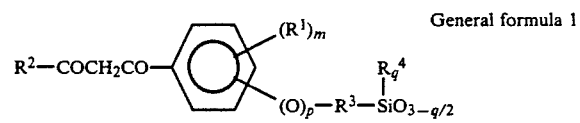

General formula 1

Herein;

$R^1$: A hydroxyl group, an alkyl group having 1 to 8 carbon atoms, or an alkoxy group having 1 to 8 carbon atoms $R^2$: An alkyl group having 1 to 7 carbon atoms $R^3$: A bivalent alkylene group or an oxyalkylene group having at least 2 carbon atoms $R^4$, $R^5$: An alkyl group, a phenyl group, or a trimethylsiloxy group having 1 to 4 carbon atoms m: An integer from 0 to 3 p: 0 or 1 q,r: An integer from 0 to 3.)

An excellent UV-A absorbing capability and compatibility with a silicone-based base are provided.

1 Claim, 3 Drawing Sheets

ALKYL-ARYL 1,3-PROPANEDIONE SILICONE DERIVATIVE AND AN EXTERNAL PREPARATION FOR SKIN WITH THE DERIVATIVE COMPOUNDED THEREIN

FIELD OF THE INVENTION

The present invention relates to an alkyl-aryl 1,3-propanedione silicone derivative and an external preparation for skin, and more particularly to improvement of ultraviolet ray absorption capability in a UV-A area.

BACKGROUND ART

From a view point of dermatology, ultraviolet ray in sunlight is divided to long wavelength ultraviolet ray (UV-A) in a range from 400 nm to 320 nm, medium wavelength ultraviolet ray (UV-B) in a range from 320 nm to 290 nm, and short wavelength ultraviolet ray (UV-C) in a range of 290 nm or less. Of these, the ultraviolet ray having a wavelength of 290 nm or less is absorbed by the ozone layer, and does not reach the surface of the earth.

Ultraviolet rays reaching the surface of the earth gives various effects to skin of a man. Of the ultraviolet rays which reach the surface of the earth, UV-B forms erythema or blister on human skin and also promotes formation of melanin. On the other hand, UV-A changes color of human skin to brown, and promotes rapid aging of human skin including decrease of elasticity thereof or generation of wrinkles on it. Also UV-A promotes start of the erythema reaction or actives this reaction in certain types of patients, and furthermore it may becomes a cause for light toxicity or allergy against light. To protect human skin from the harms of UV-A as described above, various types of ultraviolet ray absorbent have been developed.

Conventional types of UV-A ultraviolet ray absorbent such as benzophenone derivative, dibenzoyl methane derivative, and benzotriazole have been used as a UV-A absorbent, and compounded in external preparations for skin.

On the other hand, in recent years, such silicone-based bases as dimethyl siloxane having excellent water resisting property which are not easily flown away by sweat or in swimming have been widely used in external preparations for skin in which a ultraviolet absorbent is compounded. These silicone-based bases have been used largely because, in addition to their excellent water resisting property, they can easily be extended on human skin and are very comfortable and are not sticky when used.

However, the conventional types of UV-A ultraviolet ray absorbent as described above have a remarkably low compatibility with silicone-based bases.

Also, an absorbent is generally a crystalline material having a dark color, and is easily crystalized under a low temperature, or often contaminates clothes, so that a quantity of absorbent to be used is limited to a very small level and functions of the UV-A absorbent have not been fully realized.

DISCLOSURE OF THE INVENTION

The present invention was made to solve the problems in the prior art as described above, and the object is to provide a substance which is dissolved in a silicone-based base and can block ultraviolet ray in the UV-A area and an external preparations for skin in which the substance is compounded.

Inventors of the present invention made strenuous efforts to achieve the object as described above, and found out that alkyl-aryl 1,3-propanedione silicone derivative has an excellent capability to absorb UV-A as well as an excellent availability, and completed the present invention.

Namely, the alkyl-aryl 1,3-propanedione silicone derivative is siloxane having at least one unit which is expressed by the general formula 1 as shown below; characterized in that other unit, which can exist in said siloxane, is expressed by a formula of $O_{4-r/2}SiR^5_r$.

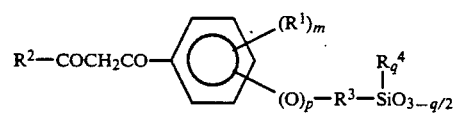

Formula 1

(herein;

$R^1$ is a hydroxyl group, or an alkyl group having 1 to 8 carbon atoms, or an alkoxy group having 1 to 8 carbon atoms, $R^2$ is an alkyl group having 1 to 7 carbon atoms, $R^3$ is a bivalent alkylene group or an oxyalkylene group having at least 2 carbon atoms, $R^4$ and $R^5$ are alkyl groups, phenyl groups, or trimethyl siloxy group, each having 1 to 4 carbon atoms, and m is an integer from 0 to 3, p is 0 or 1, and q and r are integers from 0 to 3.)

The external preparation for skin according to claim 1 is characterized in that said preparation contains one or more types of the aforesaid alkyl-aryl 1,3-propanedione silicone derivative.

More detailed description is made hereinafter for constituents of the present invention.

The alkyl-aryl 1,3-propanedione silicone derivative according to the present invention comprises a unit expressed by the formula 1 above and a formula of $O_{4-4/2} SiR^5_r$.

Examples of $R^1$ in the aforesaid general formula 1 include a hydroxyl group, an alkyl group such as a methyl group, an ethyl group, a propyl group, an isopropyl group, a butyl group, an isobutyl group, a sec-butyl group, a t-butyl group, a n-amyl group, an isoamyl group, a n-hexyl group, a 2-ethylbutyl group, an n-octyl group, and a 2ethylhexyl group, and an alkoxy group such as a methoxy group, an ethoxy group, a propoxy group, an isopropoxy group, a butoxy group, an isobutoxy group, an s-butoxy group, a t-butoxy group, an n-amyloxy group, an isoamyloxy group, an n-hexyloxy group, a 2-ethylbutoxy group, an n-pentyloxy group, an n-octyloxy group, and a 2-ethylhexyloxy group.

Also, $R^2$ may be any alkyl group as far as it has 1 to 7 carbon atoms, but especially an alkyl group having carbon atom, bonding to a carboxyl group being secondary or tertiary atom, is preferable. Especially suited examples of $R^2$ include an isopropyl group, a tert-butyl group, an ethylpropyl group, or an ethylpentyl group.

Examples of $R^3$ include $-CH_2CH_2-$, $-CH_2CH_2CH_2-$, $-CH_2CH(CH_3)CH_2-$, $-CH(CH_3)CH_2CH_2-$, $-CH_2CH_2CH(CH_3)-$, $-CH_2CH_2CH_2CH_2-$, $-CH_2CH_2OCH_2CH_2-$, a hexylene group, a cyclohexylene group, or a decylene group, and an alkylene group having 2 to 4 carbon atoms is especially preferable.

Examples of $R^4$ includes a methyl group, an ethyl group, a propyl group, an isopropyl group, a butyl group, an isobutyl group, a t-butyl group, a phenyl group, and a trimethylsiloxy group, but a methyl group or a unit, a portion of which is a phenyl group or a trimethylsiloxy group, is especially preferable because the raw materials can easily be procured.

m expresses a number of substituents and is an integer from 0 to 3. p is 0 or 1, and q expressed a number of substituents in $R^4$ and is an integer from 0 to 3.

In the siloxane unit expressed by the formula of $O_{4-r/2} SiR^5{}_r$, examples of $R^5$ include a methyl group, an ethyl group, a propyl group, an isopropyl group, a butyl group, an isobutyl group, a t-butyl group, a phenyl group, and a trimethylsiloxy group, but a methyl group, or a unit, a portion of which is a phenyl group, or a trimethylsiloxy group is especially preferable. r expresses a number of substituents in R5 and is an integer from 0 to 3.

Form of the alkyl-aryl 1,3-propanedione silicone-based derivative according to the present invention is either liquid or resin-like solid under the room temperature, and either type can be used as a UV-A absorbent.

The alkyl-aryl 1,3-propanedione silicone derivative according to the present invention can be synthesized in a two-stage reaction comprising a first stage of a Claisen condensation reaction and a second stage of hydrosilylating reaction.

First stage

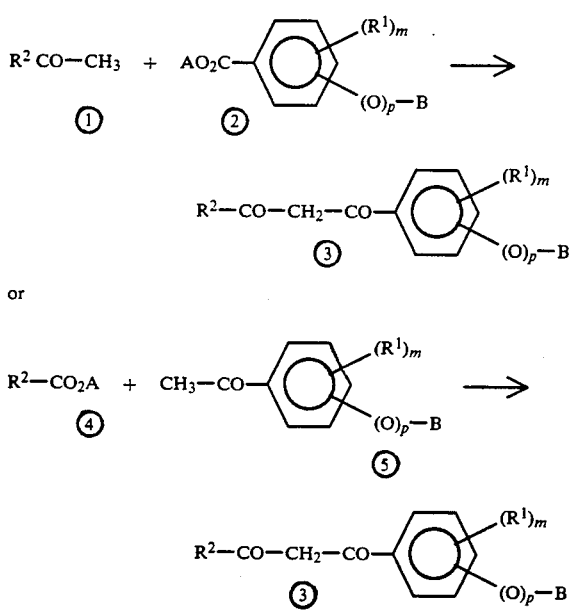

Second stage

③ +

Polysiloxane containing at least one
Si—H group in the molecule ⟶

General formula 1

It should be noted that, in the reaction formula above, $R^1, R^2$, m and p are defined by the general formula 1, A is an alkyl group having 1 to 5 carbon atoms, B is an alkenyl group or an oxyalkenyl group having at least 2 carbon atoms.

The Claisen condensation reaction in the first stage is described in R. Hauer etc., "Organic Reactions", Vo. 8, p 59, John Wiley and Sons Inc., New York, 1954, and the method was employed in the present invention.

Namely, the alkyl-aryl 1,3-propanedione derivative ③ can be obtained by reacting methylalkyl ketone ① or substituted acetophenon ⑤ to alkylester ② or ④ of fatty acid or substituted benzoic acid under the existence of a base, namely under the existence of alkali alcolate, hydride, amide compound, or hydrogenated sodium in a medium such as toluene, isopropylether, tetrahydrofuran, 1,2-dimethoxyethane, dimethylsulfoxide, or dimethylformamide under a temperature from the room temperature up to a boiling point.

The reaction in the second stage is a hydrosilylating reaction. It is known that this reaction is generally promoted by a platinum group metal, a compound of a platinum group metal, or a complex compound of said metal (Refer to Japanese Patent Laid Open Publication No. 108431/1985, Japanese Patent Laid Open Publication No. 210632/1985, and Japanese Patent Laid Open Publication No. 50711/1989).

Also, the reaction between the alkyl-aryl 1,3-Propanedione derivative 3. and polysiloxane containing at least one SiH group in the molecule is generally promoted by an ordinary catalyst such as platinum carried by carbon, acetylacetone platinum complex, platinum complex with unsaturated compound, platinum complex with unsaturated siloxane, rhodium compound and platinum compound complex.

The target alkyl-aryl 1,3-propanedione silicone derivative can be obtained by continuing this reaction in a solvent such as toluene, xylene, hexane, tetradydrofuran, tetrachloroethylene under a temperature from the room temperature up to the boiling point until SiH group disappears.

It should be noted that anything is available as a base for the external preparations for skin according to the present invention so long as the aforesaid alkyl-aryl 1,3-propanedione silicone derivative is dissolved in the material, but especially when a base based on silicone-based oil is used, the external preparations for skin smoothly extends on human skin and is very comfortable and not sticky when used, and in addition high water resisting property and hardness to be flown away by sweat or water can be obtained.

When a silicone-based base is used in the external preparations for skin according to the present invention, there is no restriction over the silicone-based base to be used, but generally such chain polysiloxane as dimethyl polysiloxane, methylpolysiloxane, methylhydrogen polysiloxane; such cyclic polysiloxane as decamethyl polysiloxane, dodecamethyl polysiloxane, tetramethyl hydrogen polysiloxane; polyether, fatty acid denatured polysiloxane, higher alcohol denatured polysiloxane, amino denatured polysiloxane can be used.

Also it should be noted that other components generally used in cosmetic such as oil, lubricant, antioxidant, surface active agent, antiseptic, sequestering agent, perfume, water, alcohol, and thickener can be added in the external preparation for skin according to the present invention according to the necessity.

There is no restriction over a form of the external preparation for skin according to the present invention, and it may be formed in any of powder, cream, paste, stick, liquid, spray, and foundation forms, and also may be emulsified by using emulsion.

The alkyl-aryl 1,3-propanedione derivative according to the present invention can fully show it effects even if it is used independently, and also the material may be used together with other UV-B absorbent such as a p-amino benzoic acid derivative like Escalole 507 (produced by Van Dyk Corp.), a P-methoxy cinnamic acid derivative like Neo Heliopan (produced by Haarmann & Reimer Gmbh.), a salicyclic acid derivative, a benzylidene camphor derivative, urocanic acid or a derivative thereof, or inorganic pigment such as titanium dioxide or zinc oxide, and furthermore together other UV-A absorbent.

A compounding ratio of the compound according to the present invention varies according to a form of the preparations as described above or a degree of required protection from ultraviolet ray, but generally the ratio is in a range from 0.1 to 20 weight %, and preferably in a range from 0.5 to 10 weight %.

PREFERRED EMBODIMENTS

Figure 1:
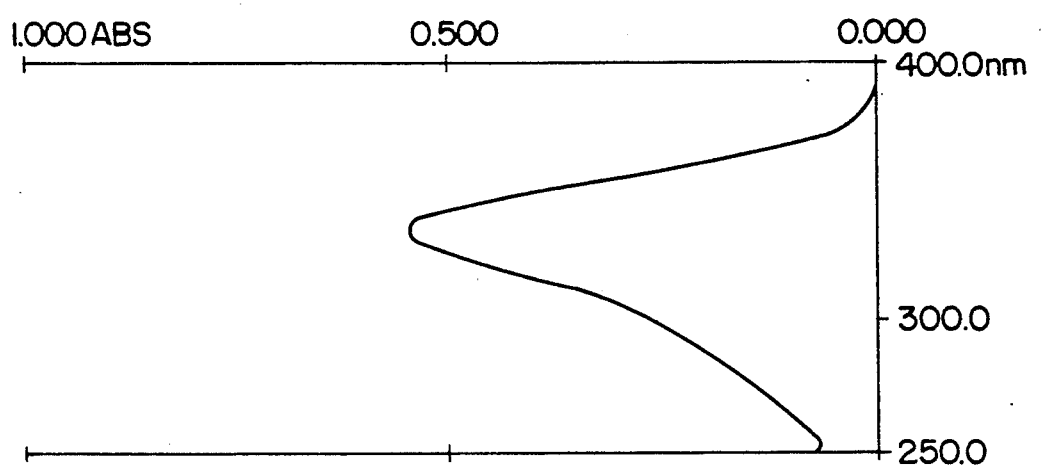
FIG. 1 is an ultraviolet ray absorption spectral map for compound 1 according to an embodiment of the present invention.

Detailed description is made hereinafter for the present invention with reference to the preferred embodiments. It should be noted that the present invention is not limited to the embodiments described herein. Unless otherwise specified, a compounding ratio is a weight %.

Characteristics and test for solubility of alkyl-aryl 1,3-propanedione silicone derivative Solubility of the following compounds 1 to 6 as examples of the alkyl-aryl 1,3-propanedione silicone derivative used in the present invention, and of 2-hydroxy-4-methoxybenzophenone (compound 1 for comparison) and 4-isopropyl dibenzoylmethane (compound 2 for comparison) was tested by using Silicone KF 56 and Silicone KF 91 (10 cs, produced by Shin'etsu Kagaku) and Squalene, all of which are silicone-bases oils.

Compound 1

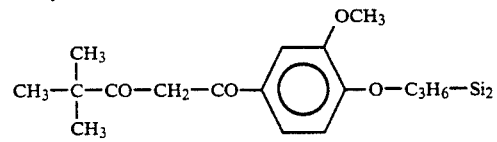

Compound 2

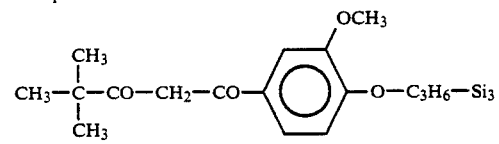

Compound 3

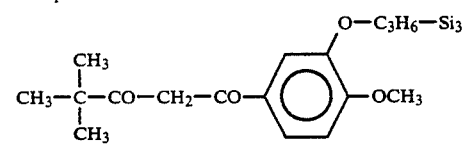

Compound 4

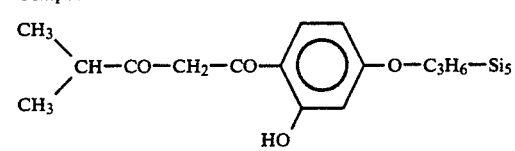

Compound 5

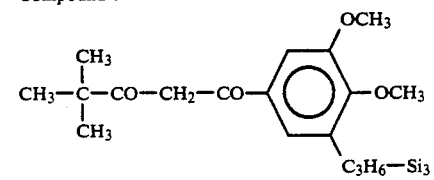

Compound 6

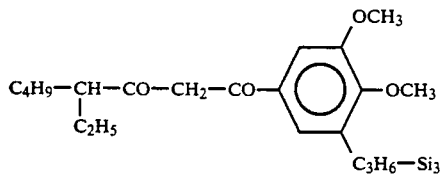

Compound 7

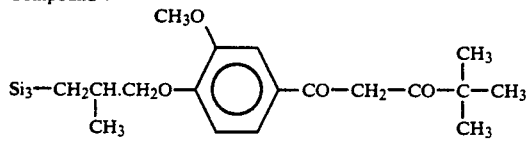

Compound 8

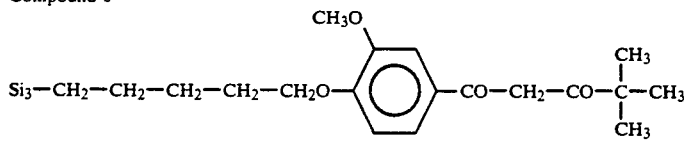

Compound 9

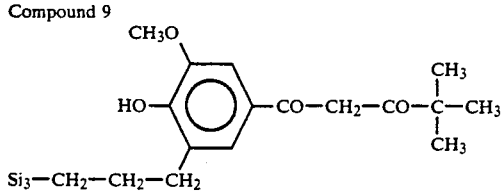

It should be noted that $Si_2$, $Si_3$, and $Si_3$ in the aforesaid compounds 1 to 6 are expressed by the following chemical formulas respectively.

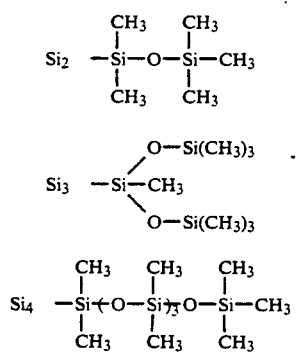

Solubility (w/w) of each compound under the room temperature (25° C.) is shown in Table 1. A circle (O) mark is put to a compound which is completely dissolved under 25° C., and a cross (X) mark is put to a compound which makes the solution cloudy even a little.

TABLE 1

| Form | | Solubility | | | | | |
|---|---|---|---|---|---|---|---|
| | | Silicon KF56 | | Sil. KF96 | | Scwr | |
| | | 30% | 50% | 30% | 50% | 30% | 50% |
| Compound 1 | Like colorless oil | O | O | O | O | O | O |
| Compound 2 | Like colorless oil | O | O | O | O | O | O |
| Compound 3 | Like colorless oil | O | O | O | O | O | O |
| Compound 4 | Like light yellow oil | O | O | O | X | O | O |
| Compound 5 | Like colorless oil | O | O | O | O | O | O |

TABLE 1-continued

| Form | | Solubility | | | | | |
|---|---|---|---|---|---|---|---|
| | | Silicon KF56 | | Sil. KF96 | | Scwr | |
| | | 30% | 50% | 30% | 50% | 30% | 50% |
| 5 | oil | | | | | | |
| Compound 6 | Like colorless oil | O | O | O | O | O | O |
| Compound 7 | Like light yellow oil | O | O | O | O | O | O |
| Compound 8 | Like light yellow oil | O | O | O | O | O | O |
| Compound 9 | Like light yellow oil | O | O | O | X | O | O |
| Compound 1 for comparison | Light yellow solid | X | X | X | X | X | X |
| Compound 2 for comparison | Light yellow solid | X | X | X | X | X | X |

From the result above, it can be understood that any of the compounds according to the present invention has excellent solubility to silicone-based base.

Test for water resisting property

The entire inside surface of a lower arm section of each of 10 male panels was carefully washed by using soap and then fully dried, and then 0.5 g of each sample liquid was applied to the entire inside surface of the lower section. Then, a 3 cm² area of the section to which the sample liquid had been applied was extracted by using 20 ml of acetonitrile, and absorption of the liquid was measured with a spectrophotometer (The result: Light absorption degree A). After extraction, operating mode of a washing machine (produced by Matsushita Denki NA-400) was set to strong vortex, and water, temperature of which had been adjusted to 30°+2° C., was continued to be released at a rate of 10

1 per minute. Then a lower arm section of a panel was steeped into water in the washing machine for 2 minutes, and then dried by a drier and extracted with acetonitrile as described above. The light absorption degree of this liquid is B. Evaluation of water resisting property was computed through the following equation and was shown with a rate of compound still remaining on the skin.

Calculation of a rate of compound remaining on the skin

Rate (%)=(Light absorption degree B/light absorption degree A)×100

The silicone derivatives 1, 2 and 5 according to the present invention were selected as sample liquid and Escalol 507 as a compound for comparison, and 3 g of each material was dissolved in 97 g of Silicone KF 56.

The rate of each compound remaining on the skin is shown in Table 2.

TABLE 2

| Panel | Sample liquid | | | |
|---|---|---|---|---|
| | No. 1 | No. 2 | No. 5 | Comparison |
| A | 97.4 | 98.9 | 98.6 | 82.3 |
| B | 95.7 | 101.3 | 101.3 | 80.6 |
| C | 97.8 | 98.6 | 98.8 | 84.5 |
| D | 97.3 | 99.3 | 99.9 | 79.8 |
| E | 96.5 | 99.3 | 99.8 | 80.3 |
| F | 98.9 | 98.9 | 99.9 | 83.8 |
| G | 95.9 | 99.3 | 102.5 | 89.2 |
| H | 96.8 | 99.9 | 101.3 | 80.4 |
| I | 97.5 | 98.9 | 97.8 | 83.9 |
| J | 96.7 | 99.4 | 99.8 | 85.1 |
| Average | 97.1 | 99.4 | 100.0 | 83.0 |

This result shows that the alkyl-aryl 1,3-propanedione silicone derivative according to the present invention is more excellent in terms of its water resisting property than the conventional ultraviolet ray absorption Escalol 507 and is not easily flown away by sweat or in washing.

Embodiment 1 Production of compound 1

0.5 mg of hexachloro-platinum (IV) hexahydrate was added in a mixture of 2.5 g of 1-(3-methoxy-4-allyloxyphenyl)-3-tert-butyl 1,3-propanedione with 1.7 g of 1,1,1,3,3-pentamethyl disiloxane and 20 ml of toluene, and the mixture was stirred for 6 hours under a temperature from 100° to 105° C. to promote the reaction. After the reaction was complete, toluene was distilled under a depressurized condition, the residue was separated and refined by a silica gel column chromatography (eluded with a 2 v/v % ethyl acetate-hexane mixture liquid), and 2.6 g of compound 1 like colorless oil was obtained. The yield was 68.4%.

An ultraviolet ray absorption spectram for compound 1 is shown in FIG. 1.

$\lambda_{max}$: 335 nm ($\epsilon$=24090)
Mass spectrum M+m/e 438

Embodiment 2 Production of compound 2

0.03 g of tetramethyl divynil disiloxane platinum complex toluene solution (containing 4 w/w % of platinum) was added in a solution in which 13.0 g of 1-(3-methoxy-4-allyloxyphenyl)-3-tert-butyl 1,3-propanedione, 11.0 g of 1,1,1,3,5,5,5-heptamethyl trisiloxane and 30 ml of toluene, and the mixture was stirred for 5 hours. After the reaction was complete, toluene was removed by distillation under a depressurized condition, the residue was separated and refined by silica gel chromatography (eluded with a 2 v/v % ethyl acetate-hexane mixture liquid), and 10.2 g of compound 2 was obtained. The yield was 47.1%.

Figure 2:
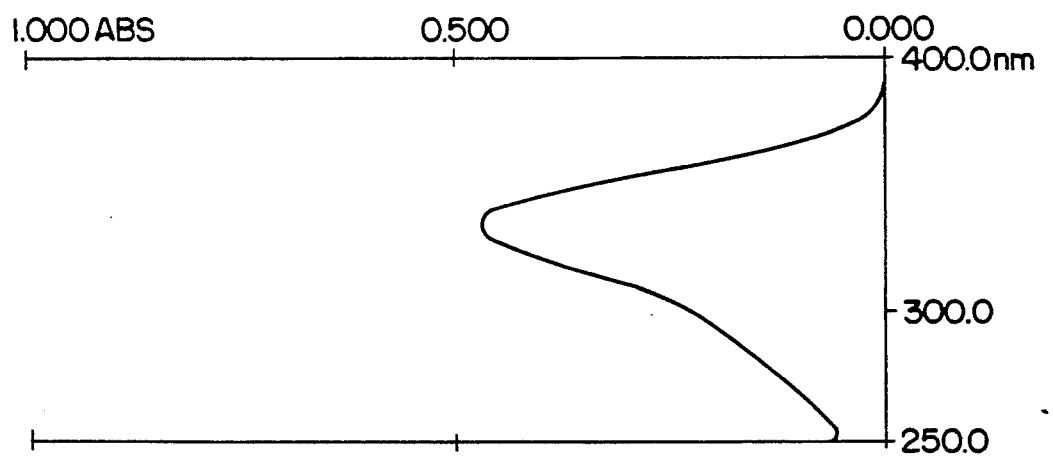
FIG. 2 is an ultraviolet ray absorption spectral map for compound 2 according to an embodiment of the present invention.

An ultraviolet ray absorption spectrum for compound 2 is shown in FIG. 2.

$\lambda_{max}$: 334 nm ($\epsilon$=23550)
Mass spectrum M+m/e 512

Embodiment 3 Production of compound 5

0.01 g of tetramethyl vinyl disiloxane platinum complex toluene solution (containing 4 w/w % platinum) was added in a solution in which 3.4 g of 1-(3-allyl-4,5-dimethoxyphenyl)-3-(1-ethylpentyl) 1,3-propanedione, 2.4 g of 1,1,1,3,5,5,5-heptamethyl trisiloxane, and 20 ml of toluene had been mixed, and the mixture was circulated for 6 hours to promote the reaction. After the reaction was complete, toluene was removed by distillation, the residue was passed through a silica gel column and eluded with 1 v/v ethyl acetate -hexane mixture solution, and 4.1 g of the compound was obtained. The yield was 73.2%.

Like colorless oil
$\lambda_{max}$: 334 nm ($\epsilon$=23500)
Mass spectrum M+m/e 568

Embodiment 4 Production of compound 7

0.05 g of the platinum catalyst described in the embodiment 2 was added in a solution in which 25.1 g of 1-{3-methoxy-4-(2-methyl-2-propenoxy) phenyl}-3-tert-butyl-,3-propanedione, 20.2 g of 1,1,1,3,5,5,5-heptamethyl trisiloxane and 50 ml of toluene had been mixed, and the mixture was left for 18 hours under a temperature in a range from 100° C. to 110° C. to promote the reaction. After the reaction was complete, toluene was removed by distillation, and compound 7 was separated and refined by distillating the residue under a depressurized condition. As a result, 28.8 g of compound 7 was obtained.

Figure 3:
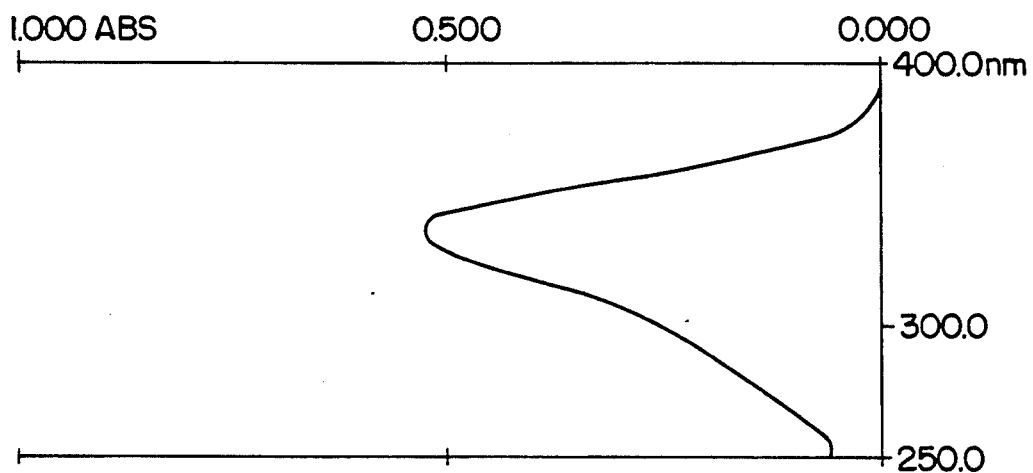
FIG. 3 is an ultraviolet ray absorption spectral map for compound 7 according to an embodiment of the present invention.

An ultraviolet ray absorption spectrum for compound 7 is shown in FIG. 3.

Light yellow oil
boiling point: in a range from bp 182° to 184° C./2 mmHg
$\lambda_{max}$: 334 nm ($\epsilon$=27350)
Mass spectrum M+m/e 526

Embodiment 5 Production of compound 8

38.7 g of 1-{3-methoxy-4-(4-pentenoxy) phenyl}-3-tert-butyl-1,3-propanedione, 29.7 g of 1,1,1,3,5,5,5-heptamethyl trisiloxane, and 0.02 g of the platinum catalyst described in embodiment 2 were dissolved in 70 ml of toluene, and the mixture was left under a temperature in a range from 95° C. to 100° C. to promote the reaction. After the reaction was complete, toluene was removed by means of distillation, the residue was distilled under a depressurized condition, and 39.7 g of the target compound 8 was obtained.

Figure 4:
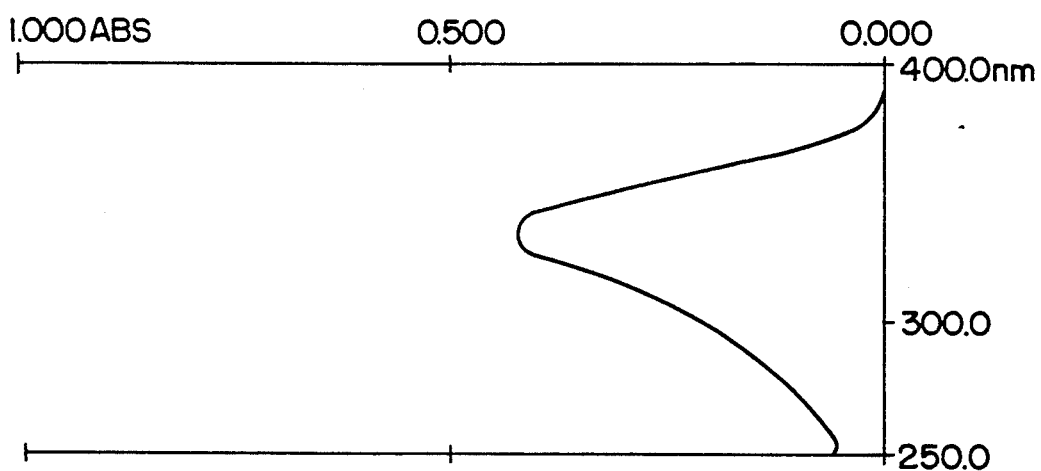
FIG. 4 is an ultraviolet ray absorption spectral map for compound 8 according to an embodiment of the present invention.

An ultraviolet ray absorption spectrum for compound 8 is shown in FIG. 4.

Light yellow oil
boiling point: from bp 215° to 225° C. (bath temperature)/2 mmHg
$\lambda_{max}$: 334 nm ($\epsilon$=23220)
Mass spectrum M+m/e 540

Embodiment 6 Production of compound 9

18.4 g of 1-(3-methoxy-4-hydroxy-5-allylphenyl)-3-tert-butyl-1,3-propanedione (light yellow crystal with a melting point of 115° to 116° C.) obtained by means of Claisen transition reaction of 1-(3-methoxy-4-allyloxyphenyl)-3-tert-butyl-1,3-propanedione, 15.5 g of 1,1,1,3,5,5,5-heptamethyl trisiloxane, and 0.02 g of the platinum catalyst described in embodiment 2 were dissolved in 50 ml of toluene, and the mixture was left for 6 hours under 100°~110° C. to promote the reaction. After the reaction was complete, toluene was removed by means of distillation, the residue was separated and refined by silica gel chromatography (eluded with 7v/v % ethyl acetate-hexane mixture liquid), and 21.7 g of compound 9 was obtained.

Figure 5:
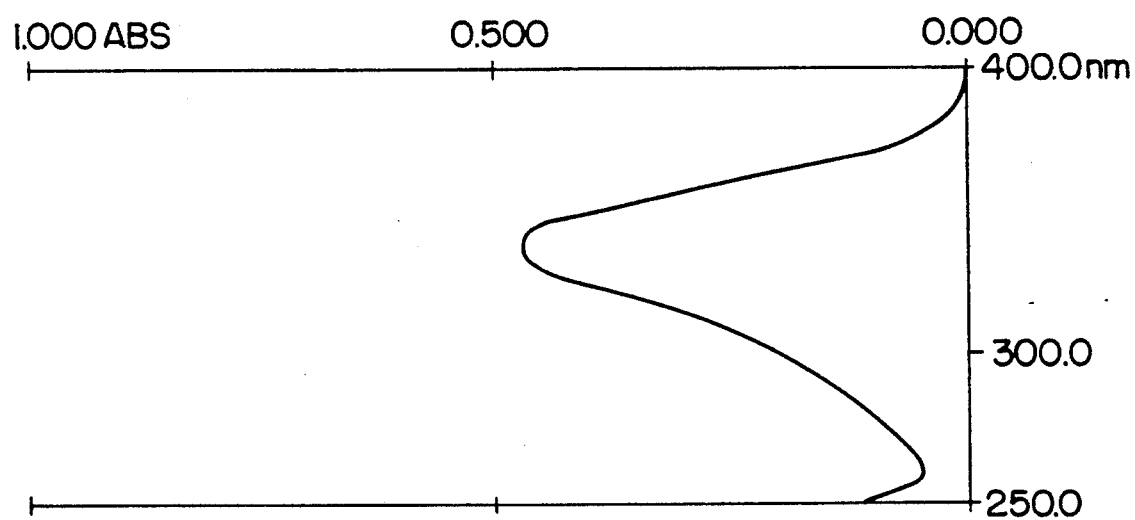
FIG. 5 is an ultraviolet ray absorption spectral map for compound 9 according to an embodiment of the present invention.

An ultraviolet ray absorption for compound 9 is shown in FIG. 5.

Light yellow solid
melting point: from 38° to 39° C.
$\lambda_{max}$: 342 nm ($\epsilon$=24000)
mass spectrum M+m/e 512

Description is made hereinafter for examples of concrete composition in the external preparation for skin according to the present invention.

| Embodiment 7 Anti-suntan cosmetic (Oily type) | |
|---|---|
| (1) Decamethyl cyclopentane siloxane | 47.0% |
| (2) Dimethyl polysiloxane (10 cs/25° C.) | 12.0% |
| (3) Methylphenyl polysiloxane (20 cs/25° C.) | 13.0% |
| (4) Silicone resin | 5.0% |
| (5) Escalol 507 | 3.0% |
| (6) Compound 2 | 20.0% |

Production (1) to (6) are mixed, fully dissolved, and then filtered, and the product is sold in the market.

Anti-suntan effect

A test for anti-suntan effect was carried out by using the antisuntan cosmetic according to embodiment 7 and a compound for comparison in which all of the compound 2 (Element (6) above) had been substituted by methylphenyl siloxane (Element (3)).

Namely, a field test was carried out in a beach, and in this test, 2 types of sample were applied to 10 panels respectively, and inquiries were made to the panels as to the anti-suntan effect and any troubles concerning their skin.

The result is shown in Table 3.

TABLE 3

| Panel | Section where sample in embod. 4 was applied | Section where compound for comp. was applied |
|---|---|---|
| A | ○ | X |
| B | ○ | △ |
| C | ○ | X |
| D | ○ | △ |
| E | ○ | X |
| F | ○ | X |
| G | △ | ○ |
| H | △ | △ |
| I | ○ | X |
| J | ○ | △ |
| Number of troubles concerning skin | None | Twitching 2 cases Itching 3 cases Eruption 1 case |

Criteria for evaluation of a degree of suntan
Visible symptoms of suntan recognized X
Symptoms of suntan recognized △
Symptoms of suntan little recognized ○

These results show that an effect of the external preparation for skin with alkylphenyl-1,3-propanedion silicone derivative compounded therein to block ultraviolet ray is higher than that of the conventional ultraviolet ray absorbent (Escalol 507), and that the external preparation for skin has a high safety without any trouble concerning human skin.

| Embodiment 8 Anti-suntan cosmetic (W/O cream) | |
|---|---|
| (1) Octamethyl cyclotetrasiloxane | 20.5% |
| (2) Dimethyl polysiloxane (100 cs) | 5.0 |
| (3) Dimethyl polysiloxane (2,500,00 cs) | 3.0 |
| (4) Fluid paraffin | 5.0 |
| (5) Polyether denatured silicone | 6.0 |
| (6) Escalol 507 | 5.0 |
| (7) Compound 5 | 4.0 |
| (8) Purified water | 43.1 |
| (9) L-glutamic acid sodium | 3.0 |
| (10) 1,3-butylene glycol | 5.0 |
| (11) Antiseptic | 0.2 |
| (12) Perfume | 0.2 |

Production (1) to (7) and (12) were mixed and dissolved under a raised temperature, and the mixture was maintained under 70° C. to form an oil phase fraction. Separately, (8) to (11) were dissolved under a raised temperature, and the mixture was maintained under 70° C. to form a water-phase fraction. The water-phase fraction was added in the oil-phase fraction, and the mixture was fully emulsified by an emulsifier. After the mixture was emulsified, the emulsion was cooled, being stirred, and when the temperature dropped to below 35° C., the emulsion was poured into a vessel and was left therein for solidification.

| Embodiment 9 Anti-Suntan cosmetic (O/W cream) | |
|---|---|
| (1) Decamethyl cyclopentane siloxane | 8.0% |
| (2) Fluid paraffin | 3.0 |
| (3) Isopropyl mirystate | 2.0 |
| (4) Vaseline | 4.0 |
| (5) Cetanol | 4.0 |
| (6) Stearic acid | 3.0 |
| (7) Glyceryl monoisostearate | 3.0 |
| (8) Neoheliopan AV | 3.0 |
| (9) Compound 1 | 1.0 |
| (10) Antiseptic | 0.2 |
| (11) Perfume | 0.2 |
| (12) Glycerin | 10.0 |
| (13) Propylene Glycol | 5.0 |
| (14) Hyaluronic acid | 0.01 |
| (15) Potassium hydroxide | 0.2 |
| (16) Purified water | 53.39 |

Production (1) to (11) were mixed to form an oil-phase fraction. Then (12) to (16) were mixed, heated to 70° C., and completely dissolved to form a water-phase fraction. The oil-phase fraction was added in the water-phase fraction and the mixture was emulsified by an emulsifier. The emulsion was cooled down to 30° C. by a heat exchanger and filled to get the product.

| Embodiment 10 Anti-suntan lotion | |
|---|---|
| (1) Dimethyl polysiloxane (5 cs) | 10.0% |
| (2) Methylphenyl polysiloxane (20 cs) | 7.0 |
| (3) Stearic acid | 1.0 |
| (4) Escalol 507 | 5.0 |

| Embodiment 10 Anti-suntan lotion | |
| --- | --- |
| (5) Compound 2 | 10.0 |
| (6) Antiseptic | 0.2 |
| (7) Perfume | 0.2 |
| (8) Glycerin | 5.0 |
| (9) Montmorillonite | 0.5 |
| (10) Potassium hydroxide | 0.2 |
| (11) Purified water | 60.9 |

Production (1) to (7) were mixed, heated under 70° C., and stirred to form an oil-phase fraction. (8) to (11) were mixed, heated to 70° C., and dissolved to a water-phase fraction. The oil-phase fraction was added in the water-phase fraction and the mixture was emulsified by an emulsifier. The emulsion was cooled down to 30° C. and was filled in a vessel to obtain the anti-suntan lotion.

| Embodiment 11 Anti-suntan dual purpose foundation | |
| --- | --- |
| (1) Silicone-treated titanium oxide | 9.5% |
| (2) Silicone-treated mica | 40.0 |
| (3) Silicone-treated talc | 20.45 |
| (4) Silicone-treated iron oxide | 7.5 |
| (5) Spheric nylon powder | 10.0 |
| (6) Trimethylor propane triisostearate | 5.0 |
| (7) Squalane | 3.0 |
| (8) Beeswax | 2.0 |
| (9) Compound 6 | 0.5 |
| (10) Sorbitane triolate | 1.0 |
| (11) Antiseptic | 0.5 |
| (12) Vitamin E | 0.05 |
| (13) Perfume | 0.5 |

Production (1) to (5) were mixed by a Henschel mixer, and then (6) to (13) were mixed, heated, and dissolved, and the resultant mixture was added in the former mixture, and the resultant new mixture was crushed and put in a plate to obtain the anti-suntan dual purpose foundation.

| Embodiment 12 Anti-suntan stick cosmetic | |
| --- | --- |
| (1) Titanium oxide | 10.0% |
| (2) Zinc oxide | 7.0 |
| (3) Mica | 16.0 |
| (4) Red iron oxide | 1.5 |
| (5) Yellow iron oxide | 1.5 |
| (6) Black iron oxide | 1.0 |
| (7) Dimethyl polysiloxane (20 cs) | 29.4 |
| (8) Trimethylolpropane-tri-2-ethylhexanoate | 8.0 |
| (9) Fluid paraffin | 7.0 |
| (10) Microcrystallin wax | 2.0 |
| (11) Ceresin | 1.0 |
| (12) Solid paraffin | 6.0 |
| (13) Escalol 507 | 5.0 |
| (14) Compound 4 | 3.0 |
| (15) Perfume | 0.5 |
| (16) Antioxidant | 0.1 |
| (17) Sorbitane sesquioleate | 1.0 |

Production (1) to (6) were mixed by a Henschel mixer, and the resultant mixture was added in another mixture obtained by mixing, stirring and dissolving (7) to (9), (13), (14), (16) and (17). Then other mixture obtained by dissolving (10) to (12) and (15) was added in the above mixture, and the resultant mixture was fully mixed and then formed into a stick-formed product.

| Embodiment 13 anti-suntan base cream | |
| --- | --- |
| (1) Dimethyl polysiloxane (2 cs) | 19.0% |
| (2) Glyceryl triisostearate | 10.0 |
| (3) Isoper G | 5.0 |
| (4) Sorbitane sesquioleate | 1.0 |
| (5) Polysiloxane ether denatured organopolysiloxane | 3.0 |
| (6) Purified water | 45.0 |
| (7) 1,3-butylene glycol | 5.0 |
| (8) Fine grain titanium oxide | 10.0 |
| (9) Pansol MCX (produced by Givaudan Co.) | 1.0 |
| (10) Compound 3 | 1.0 |
| (12) Antiseptic | q.s |
| (13) Perfume | q.s |

Production (1) to (5), (9), (10), (12) and (13) were mixed, stirred, dissolved under 70° C., and another mixture obtained by mixing and dissolving (6) to (8) and (11) and heated to 70° C. was added in the above mixture, and the resultant mixture was emulsified, dispersed, and then cooled to obtain the anti-suntan foundation.

As described above, the external preparation for skin according to the present invention can absorb ultraviolet ray in a UV-A area and is excellent in its water resisting property, and a base or other components to be compounded therein can freely be selected. Also, even if it is left under very severe conditions such as those under the burning sun, the external preparation is very stable, which is a great merit.

Also, it can well extend on human skin and is hardly flown away by sweat or water, and its effect to absorb ultraviolet ray in the UV-A area continues for a long time, which is also a preferable merit.

What is claimed is:

1. Alkyl-aryl 1,3-propanedione silicone derivative, characterized in that said derivative comprising a siloxane having at least one (1) unit expressed by the general formula 1 as shown below and another unit, which can exist in said siloxane, is expressed by a general formula of $O_{4-r/2} SiR^5_r$,

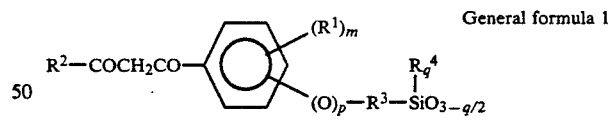

General formula 1 wherein;
R$^1$: A hydroxyl group, an alkyl group having 1 to 8 carbon atoms, or an alkoxy group having 1 to 8 carbon atoms
R$^2$: An alkyl group having 1 to 7 carbon atoms
R$^3$: A bivalent alkylene group or an oxyalkylene group having at least 2 carbon atoms
R$^4$, R$^5$: An alkyl group, a phenyl group, or a trimethylsiloxy group having 1 to 4 carbon atoms
m: An integer from 0 to 3
p: 0 or 1
q,r: An integer from 0 to 3.

* * * * *